United States Patent [19]

Zysman et al.

[11] Patent Number: 4,940,575
[45] Date of Patent: Jul. 10, 1990

[54] 4-HYDROXYISOXAZOLE DERIVATIVES, METHOD OF PREPARING SAME, AND COSMETIC AND PHARMACEUTICAL COMPOSITIONS CONTAINING THEM

[75] Inventors: Alexandre Zysman; Henri Sebag, both of Paris, France

[73] Assignee: Société Anonyme dite:L'Oreal, Paris, France

[21] Appl. No.: 371,058

[22] Filed: Jun. 26, 1989

[30] Foreign Application Priority Data

Jun. 27, 1988 [FR] France ................... 88 08612

[51] Int. Cl.$^5$ .................. A61K 31/19; A61K 31/42; A61K 31/445; C07D 261/12
[52] U.S. Cl. ...................... 424/59; 548/243; 548/248; 544/137; 544/374; 546/208; 514/236.8; 514/330
[58] Field of Search .................. 548/243, 248; 424/59; 544/137, 374; 546/208; 514/236.8, 330

[56] References Cited

U.S. PATENT DOCUMENTS 2,908,688 10/1959 Gardner et al. .
3,928,373 12/1975 Beck et al. .................... 424/59
4,447,431 5/1984 Sallmann ..................... 424/59

OTHER PUBLICATIONS

Chemical Abstracts, vol. 98, No. 11, Mar. 14, 1983, p. 584, 98:89659r.

*Primary Examiner*—Anton H. Sutto
*Assistant Examiner*—Edward C. Rosfjord
*Attorney, Agent, or Firm*—Oliff & Berridge

[57] ABSTRACT

4-Hydroxyisoxazole derivatives corresponding to the formula:

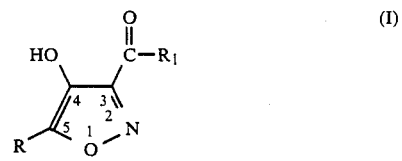

wherein:

R represents a linear or branched alkyl or hydroxyalkyl radical with 1 to 23 carbon atoms, a linear or branched alkenyl radical with 2 to 23 carbon atoms, a phenyl radical, or a benzyl radical, and $R_1$ represents $OR_2$, —$NHR_3$, or —NH—$NHR_4$, $R_2$ represents a hydrogen atom or an alkyl radical with 1 to 24 carbon atoms, $R_3$ represents a hydrogen atom, an alkyl radical with 1 to 20 carbon atoms, or a

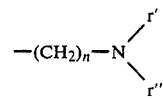

radical, where n is 2 to 3 and r' and r" are identical or different, representing a hydrogen atom or a lower alkyl radical or forming a heterocycle when taken together such as morpholine, piperidine, or piperazine, $R_4$ represents a hydrogen atom or a benzyl radical, and the salts of the formula (I) compounds.

These derivatives are applicable to therapeutic and cosmetic fields, in particular to counteract the harmful effects of the sun.

11 Claims, No Drawings

4-HYDROXYISOXAZOLE DERIVATIVES, METHOD OF PREPARING SAME, AND COSMETIC AND PHARMACEUTICAL COMPOSITIONS CONTAINING THEM

The present invention relates to new 4-hydroxyisoxazole derivatives, in particular 3,5-disubstituted derivatives, their method of preparation, and their applications in cosmetics and therapy.

The new 4-hydroxyisoxazole derivatives as defined hereinbelow are particularly appropriate for producing cosmetic compositions intended in particular to protect the skin against the harmful effects of the sun.

These derivatives have U.V. absorption covering the spectral range between 240 and 300 nm such that they constitute good sun filters against the U.V.-B type ultraviolet rays which cause inflammation or reddening of the skin when the human body is subjected to sun radiation with no special protection.

Early studies on the therapeutic properties showed that these compounds were particularly promising in the known therapeutic applications of isoxazole derivatives.

Moreover, because of their reactive functions, these 4-hydroxyisoxazole derivatives are able to form intermediates that are very useful in preparing new active compounds with potential therapeutic action.

The new 4-hydroxyisoxazole derivatives according to the invention may be represented by the following general formula:

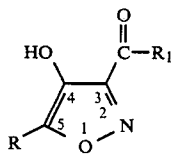

wherein:
R represents a linear or branched alkyl or hydroxyalkyl radical with 1 to 23 carbon atoms, a linear or branched alkenyl radical with 2 to 23 carbon atoms, a phenyl radical, or a benzyl radical, and
$R_1$ represents $OR_2$, $-NHR_3$, or $-NH-NHR_4$,
$R_2$ represents a hydrogen atom or an alkyl radical with 1 to 24 carbon atoms,
$R_3$ represents a hydrogen atom, an alkyl radical with 1 to 20 carbon atoms, or a

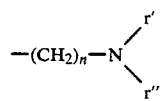

radical,
where n is 2 to 3 and r' and r" are identical or different, representing a hydrogen atom or a lower alkyl radical or form a heterocycle when taken together such as morpholine, piperidine, or piperazine,
$R_4$ represents a hydrogen atom or a benzyl radical, and the salts of the formula (I) compounds.

When radical R represents an alkyl radical with 1 to 23 carbon atoms, it is preferably an ethyl, propyl, hexyl, 2-ethylhexyl, octyl, nonyl, dodecyl, tetradecyl, or octadecyl radical.

According to a preferred embodiment of the invention, radical R is an alkyl radical with 12 to 18 carbon atoms, in particular the dodecyl, tetradecyl, or octadecyl radical.

When the compounds according to the invention are in the form of salts, they are in particular quaternary ammonium compounds obtained by quaternization of the formula (I) compounds wherein $R_1$ represents the radical $-NHR_3$, where $R_3$ represents the radical

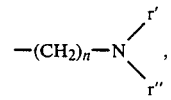

where n, r' and r" are as defined above, although the latter cannot represent a hydrogen atom.

Among the quaternizing agents one may cite in particular methyl halides, dimethyl sulfate, and methyl tosylate or mesylate.

Of the compounds particularly preferred according to the invention and corresponding to formula (I) above, the following may be mentioned:
3-methyoxycarbonyl-4-hydroxy-5-tetradecylisoxazole,
3-hydrazinocarbonyl-4-hydroxy-5-tetradecylisoxazole,
3-(N-dimethylaminoethylamido)-4-hydroxy-5-tetradecylisoxazole (and its hydrochloride),
3-[N-(2-trimethylammonio-ethyl)amido]-4-hydroxy-5-tetradecylisoxazole methylsulfate,
3-(n-butylamido)-4-hydroxy-5-tetradecylisoxazole
3-ethoxycarbonyl-4-hydroxy-5-tetradecylisoxazole, and
3-hexadecyloxycarbonyl-4-hydroxy-5-tetradecylisoxazole.

The present invention also relates to the method of preparing the formula (I) 4-hydroxyisoxazole derivatives as defined above.

This method is particularly advantageous in that it allows the compounds according to the invention to be produced in a single step with good yields.

This method, which consists of causing butyl nitrite to react on a β-ketoester (1), leads, by spontaneous cyclization resulting from dehydrogenation, to the 3-alkoxycarbonyl-4-hydroxyisoxazoles (2) according to the following reaction diagram:

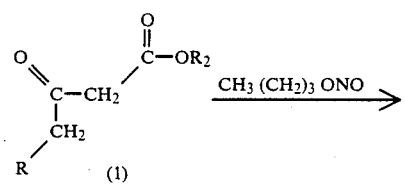

$R_2$ = Alkyl $C_1$-$C_3$

The reaction is preferably effected in solution in a solvent such as diethyl ether or diisopropyl ether with at least 3 moles of butyl nitrite per mole of β-ketoester (1) in the presence of anhydrous hydrogen chloride.

More specifically, the β-ketoester (1) and butyl nitrite are mixed in the solvent at a temperature generally below 20° C., preferably between −10° and 10° C. At this temperature, a solution of anhydrous ether saturated with hydrogen chloride is poured into the reaction mixture. As soon as addition is completed, cooling is stopped and the mixture is allowed to stand at room temperature for several hours. The 3-alkoxycarbonyl-4-hydroxyisoxazole (2) is then isolated by conventional purification methods, i.e. by distillation, crystallization, or preparative chromatography under pressure.

It has been noted that this method leads to the formation, as a byproduct, of an isomer of compounds with formula (I), corresponding to the following formula:

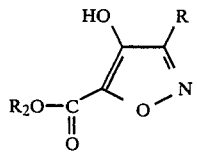

This isomer is generally formed in a proportion not exceeding 20% by weight of the reaction product obtained by the method according to the invention.

This isomer, because of the position of its substituents, does not absorb U.V. radiation in the wavelength range of interest in the field of cosmetics.

The compounds according to the invention with formula (I) wherein $R_1$ represents $-NHR_3$ and $-NH-NH-R_4$ are obtained from 3-alkoxycarbonyl-4-hydroxyisoxazoles by conventional methods.

The present invention also relates to cosmetic compositions for protection against ultraviolet radiation containing, as the active ingredient, in an acceptable cosmetic vehicle, at least one 4-hydroxyisoxazole derivative with formula (I) as defined above.

These compositions may be in the form of aqueous or water-alcohol solutions, oil solutions or emulsions, or in the form of sticks. They may also be incorporated with a propellant and constitute compositions in the aerosol form.

The cosmetic compositions according to the invention may also contain various adjuvants normally present in cosmetic sun protective compositions, namely hydrating agents, emollients or thickners, surfactants, preservatives, perfumes, or pigments.

The concentration of 4-hydroxyisoxazole derivatives in the compositions according to the invention is generally between 0.1 and 80 wt. % related to the total weight of the composition.

Several examples of methods of preparing 4-hydroxyisoxazole derivatives with formula (I) and examples of sun protective compositions will now be provided for illustration and without being limitative.

EXAMPLE 1

3-Methoxycarbonyl-4-hydroxy-5-tetradecylisoxazole

Stage 1: Preparation of methyl 3-oxooctadecanoate

Operating constantly under nitrogen, 576 g (4 moles) of Meldrum acid (2,2-dimethyl-1,3-dioxane-4,6-dione) is dissolved in 2400 cc of dichloromethane. The solution is cooled to 0° C. and 640 cc of pyridine is added dropwise.

Still at the same temperature, 1208 g (4.4 moles) of palmitoyl chloride is added in the course of one hour, then the mixture is stirred for a further hour at 0° C. Then, still at 0° C., 6000 cc of methanol is added and the mixture is kept at this temperature for 1 hour then left to stand overnight.

The next day, the mixture is refluxed for 5 hours then cooled, centrifuged, and dried. 1060 g of a white solid with a melting point of 55° C. is isolated.

Stage 2: Preparation of 3-methoxycarbonyl-4-hydroxy-5-tetradecylisoxazole 15.6 g (0.05 mole) of methyl 3-oxooctadecanoate (prepared above) and 20.6 g (0.2 mole) of butyl dissolved in 80 cc of anhydrous ether. After cooling the reaction mixture to 0° C., 200 cc of an anhydrous ether solution saturated with hydrogen chloride is added to the reaction mixture over a period of 1.5 hours. The reaction mixture is allowed to return to room temperature, with continued stirring, then left to stand overnight at the same temperature. On the next day, 8 g of 3-methoxycarbonyl-4-hydroxy-5-tetradecylisoxazole is isolated by centrifuging.

It is a white solid with a melting point of 92° C.

| Elementary Analysis: | | | |
|---|---|---|---|
| calc: | C = 67.22% | H = 9.80% | N = 4.13% |
| found: | 67.02 | 10.29 | 4.28 |

NMR $^1$H (CDCl$_3$, TMS, δ in ppm).
Characteristic signals:

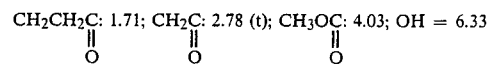

NMR $^{13}$C: (CDCl$_3$, TMS, δ in ppm).
Characteristic signals:

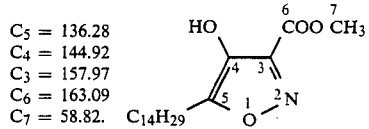

$C_5 = 136.28$
$C_4 = 144.92$
$C_3 = 157.97$
$C_6 = 163.09$
$C_7 = 58.82$.

Mass spectrum:
Mass peak by electron ionization: 339
Mass peak by chemical ionization (CH$_4$): 340
Mass peak by chemical ionization: (N$_2$O): 339
Characteristic fragment: $C_{14}H_{29}C=O$.
UV spectrum (acetonitrile): $\lambda_{max}=276$ nm, $\epsilon=2475$.

The isomer, namely 3-tetradecyl-4-hydroxy-5-methoxycarbonylisoxazole is isolated from the recrystallization filtrate.

It has the same mass peak as its isomer.
NMR $^{13}$C:
$C_5 = 139.50$
$C_4 = 145.74$
$C_3 = 156.80$
$C_6 = 159.89$
$C_7 = 52.38$

EXAMPLE 2:

3-Hydrazinocarbonyl-4-hydroxy-5-tetradecylisoxazole 13.56 g (0.04 mole) of the compound prepared in Example 1 (stage 2) is dissolved in 50 cc of chloroform. Under agitation and at room temperature, 2.2 g (0.044 mole) of hydrazine hydrate dissolved in 40 cc of isopropanol is added. The product formed precipitates gradually. After several hours of agitation, it is isolated by centrifuging. The solid is recrystallized from 200 cc of chloroform. 9.1 g of a white solid with a melting point of 130° C. is isolated.

It has a basicity index measured in acetic acid by perchloric acid of 2.9 mEq/g.

NMR $^{13}$C:
$C_5 = 133.1$
$C_4 = 150.17$
$C_3 = 156.96$
$C_6 = 158.45$ $$\text{HO} \quad \overset{6}{\text{CONH NH}_2} \atop \underset{C_{14}H_{29}}{\overset{4}{\diagup}\overset{3}{\diagdown}} \atop \underset{O}{\overset{5}{\diagdown}\overset{2}{\diagup} N}$$

UV spectrum (acetonitrile): $\lambda_{max} = 260$ nm, $\epsilon = 8136$.

EXAMPLE 3

3-(N-dimethylaminoethylamido)-4-hydroxy-5-tetradecylisoxazole Hydrochloride 30 g (0.088 mole) of the compound prepared according to Example 1 (stage 2) is dissolved at 60° C. in 300 cc of hexane. At this temperature, 7.75 g (0.088 mole) of freshly distilled 2-diemthylaminoethylamine is added. The reaction mixture if refluxed for 8 hours and the methanol formed is eliminated with a Dean Stark. After ice-cooling, the reaction mixture yields 35 g of a solid which is recrystallized from hexane.

15 g of the recrystallized solid is dissolved in 100 cc of anhydrous ether to which 5 cc of ether saturated with hydrochloric gas is added. 13 g of hydrochloride in the form of a white solid with a melting point of 77° C. is obtained.

NMR $^{13}$C:

$C_5 = 134.89$
$C_4 = 147.51$
$C_3 = 158.26$
$C_6 = 162.06$
$C_7 = 34.46$
$C_8 = 56.96$
$C_{9,10} = 43.72$

HO — $\overset{6}{\text{CONHCH}_2\text{CH}_2\text{N}}\overset{\text{CH}_3}{\underset{\text{CH}_3}{\diagdown}}$, HCl UV spectrum (acetonitrile): $\lambda_{max} = 272$ nm, $\epsilon = 2571$

EXAMPLE 4

3-[N-(2-trimethylammonio-ethyl)amido]-4-hydroxy-5-tetradecylisoxazole methylsulfate 10 g (0.025 mole) of the compound prepared according to Example 3, isolated before acidification with hydrochloric acid, is dissolved in 90 cc of anhydrous acetone. 3.2 g (0.025 mole) of dimethyl sulfate is added within 30 minutes to this solution at 40° C. Agitation is maintained at this temperature for 1 hour then the mixture is left to stand overnight. After ice-cooling, the precipitate formed is isolated by filtration. 11.1 g of a white solid is obtained.

NMR $^{13}$C:

$C_5 = 135.07$
$C_4 = 147.18$
$C_3 = 158.03$
$C_6 = 162.07$
$C_7 = 33.85$
$C_8 = 64.58$
$C_{9,10,11} = 53.71$
$C_{12} = 54.58$

HO — CONHCH$_2$CH$_2$N(CH$_3$)$_3$ CH$_3$SO$_4^\ominus$

UV spectrum (acetonitrile): $\lambda_{max} = 280$ nm, $\epsilon = 3506$.

EXAMPLE 5

3-(n-butylamido)-4-hydroxy-5-tetradecylisoxazole 10 g (0.029 mole) of the compound prepared in Example 1 (stage 2) is dissolved at 60° C. in 100 cc of hexane. 5 g (0.068 mole) of n-butylamine is added at this temperature and then the reaction mixture is heated for 5 hours at the solvent reflux. The excess butylamine together with the solvent are then eliminated by evaporation under vacuum.

The distillation residue is subjected to HPLC (dichloromethane:hexane) on silica. 8.8 g of a white solid with a melting point of 64° C. is isolated.

NMR $^{13}$C:

$C_5 = 136.22$
$C_4 = 145.94$
$C_3 = 156.79$
$C_6 = 161.90$
$C_7 = 38.85$
$C_8 = 31.40$
$C_9 = 20.01$
$C_{10} = 13.65$

HO — CONHCH$_2$CH$_2$CH$_2$CH$_3$

UV spectrum (acetonitrile): $\lambda_{max} = 280$ nm, $\epsilon = 4064$.

EXAMPLE 6

3-ethylcarbethoxy-4-hydroxy-5-tetradecylisoxazole 20 g (0.059 mole) of the mixture of iosmers obtained according to Example 1 (stage 2) is dissolved in 1000 ml of absolute ethanol. This solution, after addition of 20 ml of H$_2$SO$_4$ (8 N) is refluxed for about ten hours. 250 ml of water and 100 ml of H$_2$SO$_4$ (8 N) are then added and evaporated under vacuum. The solution is extracted twice with 250 ml of dichloromethane. After drying over sodium sulfate, the solvent is eliminated at reduced pressure. The residue is subjected to HPLC on silica with dichloromethane as the eluent. 12.2 g of a white solid with a melting point of 54° C. is isolated.

NMR $^{13}$C: (CDCl$_3$, TMS, $\delta$ in ppm)

$C_5 = 136.35$
$C_4 = 145.03$
$C_3 = 157.87$
$C_6 = 162.82$
$C_7 = 62.54$
$C_8 = 14.13$

HO — COOCH$_2$CH$_3$

UV spectrum (acetonitrile): $\lambda_{max} = 280$ nm, $\epsilon = 2475$.

EXAMPLE 7

3-hexadecyloxycarbonbyl-4-hydroxy-5-tetradecylisoxazole 1.7 g (0.005 mole) of the isomer mixture obtained in Example 1 (stage 2) is dissolved in 15 ml of anhydrous toluene. 3.6 g (0.015 mole) of hexadecanol and 0.076 g of para-toluenesulfonic acid is added to this solution. After cooling, the mixture deposits a solid which is recrystallized in ethyl acetate. 2 g of a white solid with a melting point of 70° C. is isolated.

NMR $^{13}$C: (CDCl$_3$, TMS, $\delta$ in ppm)

$C_5 = 136.36$
$C_4 = 145.01$
$C_3 = 157.79$
$C_6 = 162.92$
$C_7 = 66.59$

HO — CO$_2$CH$_2$(CH$_2$)$_{14}$CH$_3$

UV spectrum (acetonitrile): $\lambda_{max} = 280$ nm, $\epsilon = 3206$.

SAMPLE COMPOSITIONS

EXAMPLE A

Sun protective cream in the form of an oil-in-water emulsion.

| | |
|---|---|
| 3-ethoxycarbonyl-4-hydroxy-5-tetradecyl-isoxazole | 3 g |
| Mixture of cetyl and stearyl alcohols with 33 moles of ethylene oxide sold under the name Sinnowax AO by the Henkel Company | 7.5 g |
| Mixture of glycerol mono- and distearate sold under the name of Geleol Copeaux by the Gattefosse Company | 2 g |
| Cetyl alcohol | 1.8 g |
| Benzoate of $C_{12}$ to $C_{15}$ alcohols sold under the name Finsolv TN by the Finetex Company | 10 g |
| Isopropyl myristate | 2.2 g |
| Glycerine | 7 g |
| Propylene glycol | 3 g |
| Preservatives | 0.4 g |
| Deionized water, to make: | 100 g |

EXAMPLE B

Sun protective oil

| | |
|---|---|
| 3-ethoxycarbonyl-4-hydroxy-5-tetradecylisoxazole | 2 g |
| Benzoate of $C_{12}$ to $C_{15}$ alcohols sold under the name Finsolv TN by the Finetex Company | 30 g |
| 2-Ethylhexyl cocoate | 12 g |
| Colza oil | 10 g |
| Cyclotetradimethylsiloxane sold under the name Abil K4 by the Goldschmidt Company | 14 g |
| Antioxidant | 0.04 g |
| Sunflower oil, to make: | 100 g |

What is claimed is:

1. Derivatives of 4-hydroxyisoxazoles having the formula:

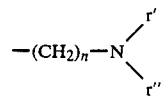

(I)

wherein:
R represents a linear or branched alkyl or hydroxyalkyl radical with 1 to 23 carbon atoms, a linear or branched alkenyl radical with 2 to 23 carbon atoms, a phenyl radical, or a benzyl radical, and
$R_1$ represents $OR_2$, $-NHR_3$, or $-NH-NHR_4$,
$R_2$ represents a hydrogen atom or an alkyl radical with 1 to 24 carbon atoms,
$R_3$ represents a hydrogen atom, an alkyl radical with 1 to 20 carbon atoms, or a

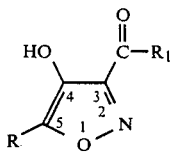

radical, where n is 2 to 3 and r' and r" are identical or different, representing a hydrogen atom or a lower alkyl radical or forming a morpholine, piperidine, or piperazine when taken together,
$R_4$ represents a hydrogen atom or a benzyl radical,
and salts of the formula (I) compounds.

2. Compounds according to claim 1 wherein R represents ethyl, propyl, hexyl, 2-ethylhexyl, octyl, nonyl, dodecyl, tetradecyl, or octadecyl radical.

3. Compounds according to claim 1, being in the form of a quaternary ammonium salt in which $R_1$ represents the radical $-NH-R_3$, where $R_3$ is the radical

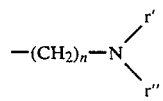

where n, r' and r" are as defined in claim 1 except that r" does not represent a hydrogen atom.

4. Compounds according to claim 1, selected from the group consisting of:
3-methoxycarbonyl-4-hydroxy-5-tetradecylisoxazole,
3-hydrazinocarbonyl-4-hydroxy-5-tetradecylisoxazole,
3-(N-dimethylaminoethylamido)-4-hydroxy-5-tetradecylisoxazole,
3-[N-(2-trimethylammonio-ethyl)amido]-4hydroxy-5-tetradecylisoxazole methylsulfate,
3-(n-butylamido)-4-hydroxy-5-tetradecylisoxazole,
3-ethoxycarbonyl-4-hydroxy-5-tetradecylisoxazole, and
3-hexadecyloxycarbonyl-4-hydroxy-5-tetradecylisoxazole.

5. Method of preparing derivatives of 4-hydroxyisoxazoles of the formula

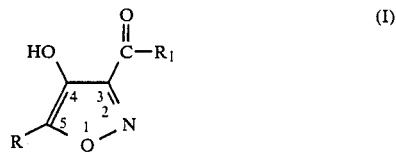

wherein:
R represents a linear or branched alkyl or hydroxyalkyl radical with 1 to 23 carbon atoms, a linear or branched alkenyl radical with 2 to 23 carbon atoms, a phenyl radical, or a benzyl radical, and
$R_1$ represents $OR_2$, $-NHR_3$, or $-NH-NHR_4$,
$R_2$ represents a hydrogen atom or an alkyl radical with 1 to 24 carbon atoms,
$R_3$ represents a hydrogen atom, an alkyl radical with 1 to 20 carbon atoms, or a

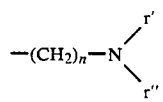

radical,
where n is 2 to 3 and r' and r" are identical or different, representing a hydrogen atom or a lower alkyl radical or form a morpholine, piperidine, or piperazine when taken together,
$R_4$ represents a hydrogen atom or a benzyl radical, and the salts of the formula (I) compounds, comprising reacting butyl nitrite with a β ketoester of the formula:

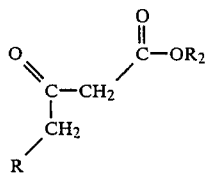

wherein:

$R_2$ represents a lower alkyl radical with 1 to 3 carbon atoms to obtain a 3-alkoxycarbonyl-4-hydroxyisoxazole of the formula

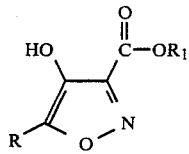

6. Method according to claim 5 wherein the reaction is carried out in diethyl or diisopropyl ether with at least 3 moles of butyl nitrite per mole of β-ketoester in the presence of anhydrous hydrochloric gas.

7. Method according to claim 5, wherein the reaction is carried out at a temperature lower than 20° C.

8. Sun protective cosmetic composition, comprising and acceptable cosmetic vehicle and at least one compound of the formula (I);

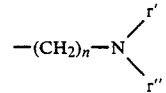

wherein
R represents a linear or branched alkyl or hydroxyalkyl radical with 1 to 23 carbon atoms, a linear or branched alkenyl radical with 2 to 23 carbon atoms, a phenyl radical, or a benzyl radical, and
$R_1$ represents $OR_2$, $-NHR_3$, or $-NH-NHR_4$,
$R_2$ represents a hydrogen atom or an alkyl radical with 1 to 24 carbon atoms,
$R_3$ represents a hydrogen atom, an alkyl radical with 1 to 20 carbon atoms, or a $$-(CH_2)_n-N\diagdown_{r''}^{r'}$$

radical,
where n is 2 to 3 and r' and r'' are identical or different, representing a hydrogen atom or a lower alkyl radical or form a morpholine, piperidine, or piperazine when taken together,
$R_4$ represents a hydrogen atom or a benzyl radical, and the salts of the formula (I) compounds.

9. Composition according to claim 8 wherein the compound of formula (I), or one of its salts is present in a concentration between 0.1 and 80 wt. % with respect to the total weight of the composition.

10. Method according to claim 5, wherein the ester function of said 3-alkoxycarbonyl-4-hydroxyisoxazole is converted to another meaning listed for $R_1$.

11. Method according to claim 7, wherein said temperature is between −10° and 10° C.

* * * * *